United States Patent
Crisci et al.

(10) Patent No.: US 6,414,057 B1
(45) Date of Patent: Jul. 2, 2002

(54) PHOTOCHROMATIC COMPOUNDS, PROCESS FOR THEIR PREPARATION AND THEIR USE IN POLYMERIC MATERIALS

(75) Inventors: Luciana Crisci, Graffignana; William Giroldini, San Donato; Vincenzo Malatesta, San Maurizio; Maria Lucia Wis, Milano, all of (IT)

(73) Assignee: Great Lakes Chemical (Europe) GmbH, Frauenfeld (CH)

( * ) Notice: Subject to any disclaimer, the term of this patent is extended or adjusted under 35 U.S.C. 154(b) by 0 days.

(21) Appl. No.: 09/446,904
(22) PCT Filed: Jul. 1, 1998
(86) PCT No.: PCT/EP98/03994
§ 371 (c)(1), (2), (4) Date: Mar. 6, 2000
(87) PCT Pub. No.: WO99/01457
PCT Pub. Date: Jan. 14, 1999

(30) Foreign Application Priority Data

Jul. 3, 1997 (IT) .......................... MI97A1573

(51) Int. Cl.[7] .............................. C08K 5/34; G02B 5/23
(52) U.S. Cl. ..................... 524/89; 252/583; 252/586; 544/71; 524/90
(58) Field of Search ................. 252/583, 586; 544/71; 524/89, 90

(56) References Cited

U.S. PATENT DOCUMENTS 5,730,908 A * 3/1998 Nodari et al. ............. 252/586

FOREIGN PATENT DOCUMENTS

| EP | 134633 | * | 1/1985 |
| EP | 432841 | * | 6/1991 |
| EP | 508219 | * | 10/1992 |
| EP | 524692 | * | 1/1993 |

* cited by examiner

*Primary Examiner*—Kriellion A. Sanders
(74) *Attorney, Agent, or Firm*—Oblon, Spivak, McClelland, Maier & Neustadt, P.C.

(57) ABSTRACT

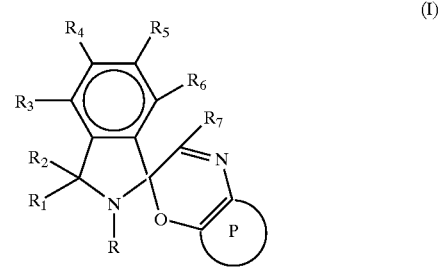

Photochromic compounds belonging to the group of spiro-isoindolino-oxazines having general formula (I). The above photochromatic compounds having general formula (I) have excellent photochromic characteristics, excellent stress resistance and high dyability characteristics.

21 Claims, No Drawings

PHOTOCHROMATIC COMPOUNDS, PROCESS FOR THEIR PREPARATION AND THEIR USE IN POLYMERIC MATERIALS

The present invention relates to photochromatic compounds.

More specifically, the present invention relates to photochromatic compounds belonging to the group of spiro-isoindolino-oxazines, a process for their preparation and their use in polymeric materials.

A further object of the present invention relates to polymeric compositions containing said photochromatic compounds and the photochromatic articles obtained from their processing.

Photochromatic compounds are substances which have the characteristic of reversibly changing colour and/or degree of light transmission when exposed to solar or artificial light in the band ranging from UV to visible, or to some types of electromagnetic radiation, returning to their original state of colour and transmission when the initial light source is removed.

There are numerous substances with photochromatic characteristics, which belong to various groups of both organic and inorganic compounds such as, for example, those described in the texts "Photochromism", by G. H. Brown (Ed.), Vol. III of the Weissberger series "Techniques of Organic Chemistry", Wiley Interscience, New York (1971) and in "Photochromsim: Molecules and Systems", by H. Duerr and H. Bouas-Laurent (Ed.), Vol. 40 of the series "Studies in Organic Chemistry" Elsevier (1990).

Among organic photochromatic compounds, those belonging to the groups of spiro-indolino-oxazines, spiropyranes and chromenes, are particularly known and used.

The above compounds are capable of giving photochromatic characteristics to polymerized organic materials used, for example, in the production of photochromatic lenses for eye-glasses, special inks, toys, and in many other applications.

As an example, the following patents can be mentioned: U.S. Pat. Nos. 3,562,172, 3,578,602, 4,215.010, 4,342,668, 5,055,576, 5,110,922, 5,186,867, EP 146.135, EP 134.633, EP 141.407, EP 245.020, IT 1.223.348 and IT 1.238.694.

Compounds belonging to the group of spiro-indolino-oxazines have, with respect to other known compounds such as, for example, compounds belonging to the group of spiro-pyranes, the advantage of having a much higher stress resistance when subjected to light and darkness cycles and also have good dyability characteristics.

The Applicant has now found photochromatic compounds belonging to the group of spiro-isoindolino-oxazines which have excellent photochromatic characteristics, excellent stress resistance and high dyability characteristics.

The present invention therefore relates to photochromatic compounds belonging to the group of spiro-isoindolino-oxazines having general formula (I):

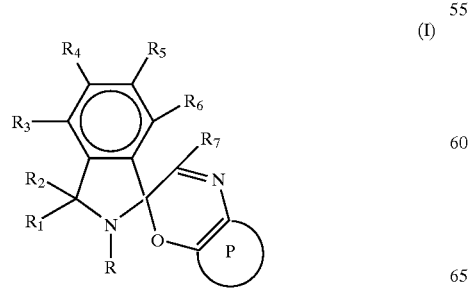

(I)

wherein:

a) R represents a linear or branched $C_1-C_{10}$ alkyl group, said alkyl group optionally substituted with 1–10 halogen atoms selected from fluorine, chlorine and bromine, or with hydroxyl groups, linear or branched $C_1-C_6$ alkoxyl groups, carboxyl groups, cyano groups, or with a 2,2,6,6-tetramethylpiperidine group; a linear or branched $C_2-C_6$ alkenyl group; an aryl group selected from phenyl, biphenyl and naphthyl, said aryl group optionally substituted with linear or branched ($C_1-C_6$) alkoxyl groups, carboxyl groups, amine groups, N,N-dialkyl ($C_1-C_6$) amine groups; a benzyl group;

b) $R_1$ and $R_2$, the same or different, represent a linear or branched $C_1-C_{10}$ alkyl group, said alkyl group optionally substituted with 1–10 halogen atoms selected from fluorine, chlorine and bromine, or with hydroxyl groups, linear or branched $C_1-C_6$ alkoxyl groups, carboxyl groups, cyano groups; a linear or branched $C_2-C_{10}$ alkenyl group; a benzyl group; a linear or branched $C_1-C_6$ alkoxyl group; an N-alkyl ($C_1-C_6$) amine group; an N,N-dialkyl ($C_1-C_6$) amine group; or $R_1$ and $R_2$, considered jointly with the carbon atom to which they are bound, represent a $C_4-C_{10}$ cycloalkyl group, said cycloalkyl group optionally substituted with halogen atoms selected from fluorine, chlorine and bromine, or with hydroxyl groups, linear or branched $C_1-C_6$ alkoxyl groups, carboxyl groups, cyano groups, amine groups, N-alkyl ($C_1-C_6$) amine groups, N,N-dialkyl ($C_1-C_6$) amine groups; an N,N-dialkyl ($C_1-C_6$) amide group; a cyano group; an aryl group selected from phenyl and biphenyl;

c) $R_3$, $R_4$, $R_5$ and $R_6$ the same or different, represent a hydrogen atom; a halogen atom selected from fluorine, chlorine, bromine and iodine; a linear or branched $C_1-C_6$ alkyl group, said alkyl group optionally substituted with 1–6 halogen atoms selected from fluorine, chlorine and bromine, or with hydroxyl groups, linear or branched $C_1-C_6$ alkoxyl groups, cyano groups; a benzyl group; a hydroxyl group; a linear or branched $C_1-C_6$ alkoxyl group; an amine group; an N-alkyl ($C_1-C_6$) amine group; an N,N-dialkyl ($C_1-C_6$) amine group; a piperidine, piperazine or morpholine group; a $C_1-C_6$ carboxyalkyl group; a $C_2-C_6$ carboxyalkenyl group; a carboxyamide group; an N-alkyl ($C_1-C_6$) carboxyamide group; an N,N-dialkyl ($C_1-C_6$) carboxyamide group; a cyano group; a nitro group; a sulfonic group; an aryl group selected from phenyl, biphenyl and naphthyl, said aryl group optionally substituted with N,N-dialkyl ($C_1-C_6$) amine groups, linear or branched $C_1-C_6$ alkoxyl groups, hydroxyl groups, linear or branched $C_1-C_6$ alkyl groups; an acyl group of the alkyl ketone, aryl ketone or benzyl ketone type; a linear or branched $C_2-C_6$ alkenyl group, said alkenyl group optionally subsituted with one or two N,N-dialkyl ($C_1-C_6$) 4-aniline groups; an N-2,3-dihydroindoline group; a linear or branched $C_1-C_6$ thioether group;

d) two consecutive substituents between $R_3$ and $R_6$, can represent condensation points with other aromatic, heterocyclic or quinonic rings;

e) $R_7$ represents a hydrogen atom; a halogen atom selected from fluorine, chlorine and bromine; a linear or branched $C_1$–$C_6$ alkyl group; a linear or branched $C_1$–$C_6$ alkoxyl group; a phenyl group; a phenoxyl group;

f) P represents a monocyclic or polycyclic aromatic nucleus, belonging to one of the following types: benzenic represented by general formula (II); naphthalenic represented by general formula (III); quinolinic represented by general formula (IV); isoquinolinic represented by general formula (V); cumarinic represented by general formula (VI); quinazolinic represented by general formula (VII); phenanthrenic represented by general formula (VIII); anthracenic represented by general formula (IX):

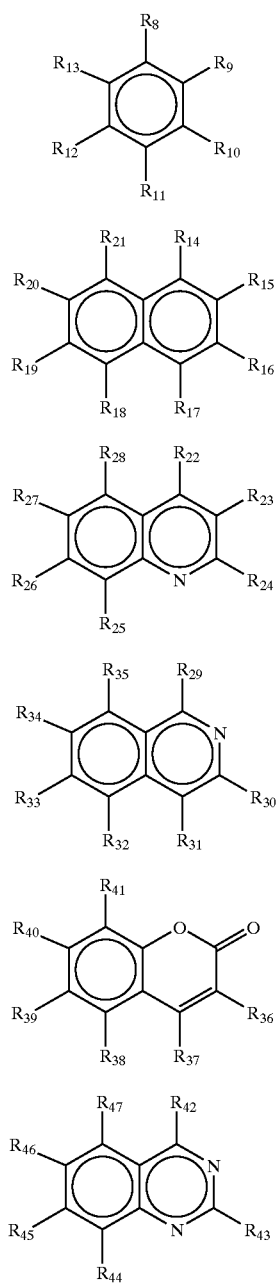

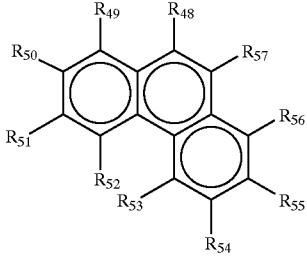

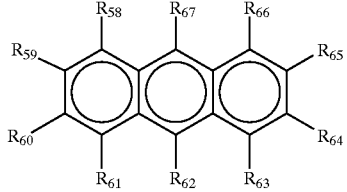

wherein:
at least two adjacent substituents between $R_8$ and $R_{13}$, $R_{14}$ and $R_{21}$, $R_{22}$ and $R_{28}$, $R_{30}$ and $R_{35}$, $R_{36}$ and $R_{41}$, $R_{44}$ and $R_{47}$, $R_{48}$ and $R_{57}$, $R_{58}$ and $R_{67}$, represent the condensation points with the oxazine ring, the other substituents having the same meaning described under point c).

Preferred compounds having general formula (I) for the purposes of the present invention are those in which:

R represents one of the following groups: methyl, ethyl, isopropyl, 2-allyl, 2-hydroxyethyl, 2-carboxymethyl, phenyl, 4-N,N-dimethylaminoaniline, 4-methoxybenzene, 4-cyanobenzene;

$R_1$ and $R_2$, the same or different, represent a methyl or phenyl group; or considered jointly with the carbon atom to which they are bound, represent a cyclohexyl group;

$R_3$, $R_4$, $R_5$ and $R_6$, the same or different, represent a hydrogen atom, a fluorine atom, a chlorine atom, a bromine atom, or one of the following groups: methyl, isopropyl, hydroxyl, methoxyl, N,N-dimethylamine, piperidine, morpholine, carboxyl, carboxymethyl, N,N-dimethylcarboxyamide, cyano, nitro, methylketone, phenylketone, phenyl;

$R_7$ represents a hydrogen atom, a chlorine atom, a bromine atom, a methyl group or a phenyl group;

P represents one of the groups having general formula (II) to (IX), wherein:

i) two adjacent substituents between $R_8$ and $R_{13}$, $R_{14}$ and $R_{21}$, $R_{22}$ and $R_{28}$, $R_{30}$ and $R_{35}$, $R_{36}$ and $R_{41}$, $R_{44}$ and $R_{47}$, $R_{48}$ and $R_{57}$, $R_{58}$ and $R_{67}$, independently represent the condensation point with the oxazine ring and the other substituents each independently represent a hydrogen atom, a fluorine atom, a chlorine atom, a bromine atom, or one of the following groups: methyl, isopropyl, hydroxyl, methoxyl, 2-hydroxyethyl, 2-allyl, piperidine, morpholine, N,N-dimethylamine, carboxyl, carboxymethyl, N,N-dimethylcarboxyamide, cyano, nitro, methylketone, ethylketone, phenylketone, methylthiol;

ii) two adjacent substituents between $R_8$ and $R_{13}$, $R_{14}$ and $R_{21}$, $R_{22}$ and $R_{28}$, $R_{30}$ and $R_{35}$, $R_{36}$ and $R_{41}$, $R_{44}$ and $R_{47}$, $R_{48}$ and $R_{57}$, $R_{58}$ and $R_{67}$, different from those specified under point i), represent the condensation point with a benzene or quinone ring.

Specific examples of preferred compounds of the present invention are:

Compound having formula (Ia):

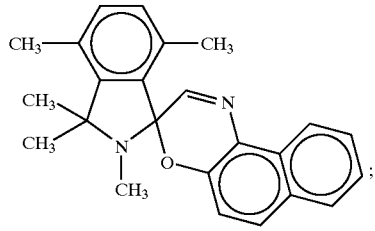
(Ia)

Compound having formula (Ib):

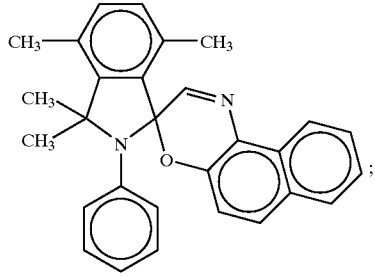
(Ib)

Compound having formula (Ic):

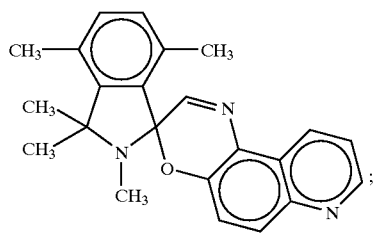
(Ic)

Compound having formula (Id):

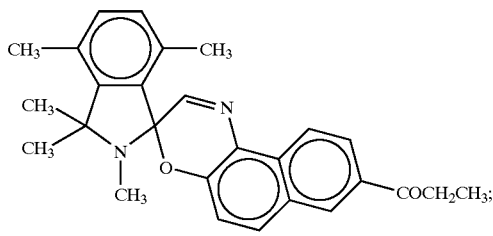
(Id)

Compound having formula (Ie):

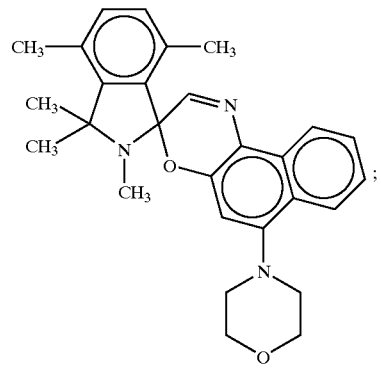
(Ie)

Compound having formula (If):

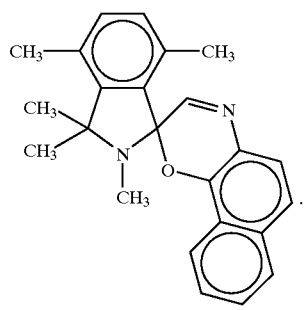
(If)

A further object of the present invention relates to a process for the preparation of the photochromatic compounds having general formula (I).

The photochromatic compounds having general formula (I) can be prepared by the condensation of isoindoline compounds having general formula (X):

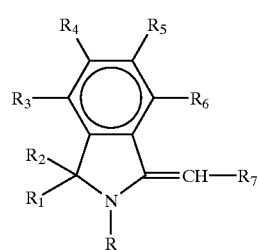
(X)

wherein the substituents from R to $R_7$ have the same meanings described above, with nitrous compounds having general formula (XI):

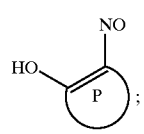
(XI)

or with aromatic 1,2-quinones having general formula (XII):

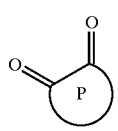

(XII)

wherein P has the same meanings described above.

The condensation reaction between the isoindoline compounds having general formula (X) and the nitrous compounds having general formula (XI), illustrated in Scheme I

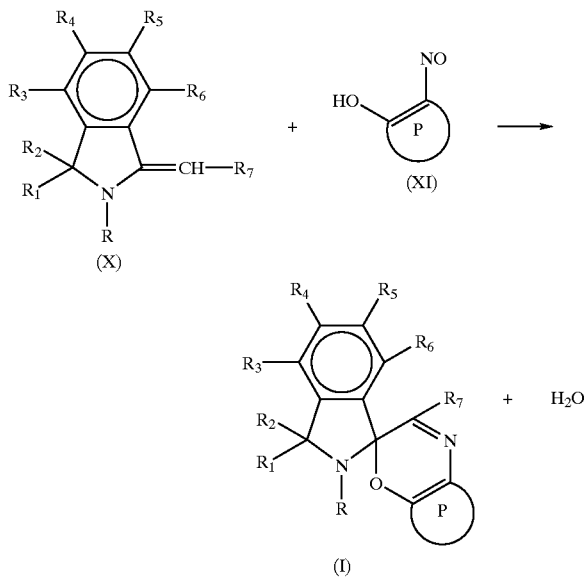

is carried out in the presence of an inert organic solvent such as, for example, ethyl alcohol, isopropanol, toluene, or a mixture of these solvents, at a temperature ranging from 50° C. to 100° C., preferably between 60° C. and 75° C., for a time ranging from 1 hour to 10 hours, preferably between 2 hours and 5 hours. The reaction product thus obtained is, generally, purified by elution on a silica column and subsequent crystallization from a solvent such as, for example, acetone, toluene, heptane.

The condensation reaction between the isoindoline compounds having general formula (X) and the aromatic 1,2-quinones having general formula (XII), illustrated in Scheme 2:

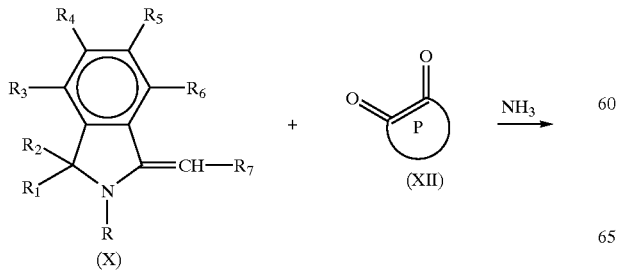

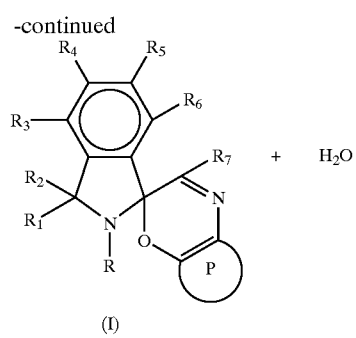

is carried out in the presence of an inert organic solvent such as, for example, ethyl alcohol, isopropanol, toluene, or a mixture of these solvents, and in the presence of aqueous ammonia at 30%, at a temperature ranging from 50° C. to 100° C., preferably between 60° C. and 75° C., for a time ranging from 1 hour to 10 hours, preferably between 2 hours and 3 hours. The reaction product thus obtained is, generally, purified by elution on a silica column and subsequent crystallization from a solvent such as, for example, acetone, toluene, heptane.

The isoindoline compounds having general formula (X) can be prepared according to procedures known in the art and described, for example, in: "Tetrahedron" (1966), Vol. 22, page 2481; "Journal of Organic Chemistry" (1979), Vol. 44, page 1519; "Angewandte Chemie International (1968), Vol. 7, page 373.

The isoindoline compounds having general formula (X) are usually kept in the form of salts such as, for example, iodides, bromides, chlorides, as the tree base is easily oxidated by the air.

The nitrous compounds having general formula (XI) can be prepared by the reaction of phenol compounds with nitrous acid or butyl nitrite, as described, for example, in Italian patent 1.176.858.

The aromatic 1,2-quinones having general formula (XII) can be prepared as described, for example, in: "Journal of American Chemical Society" (1952), Vol. 74, page 278; Chemical Abstract 103–104923q; in European patent EP 245.020 and in U.S. Pat. No. 5,446,150.

Specific examples of isoindoline compounds having general formula (X) are the following, represented by formula (Xa) corresponding to 1,1,2,4,7-pentamethyl-3-methylene-isoindoline and formula (Xb) corresponding to 1,1,4,7-tetramethyl-N-phenyl-3-methylene-isoindoline:

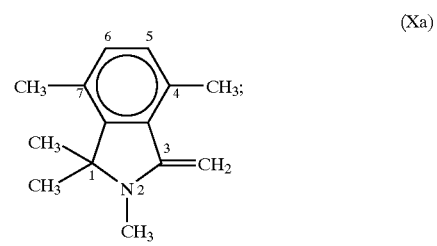

-continued (Xb)

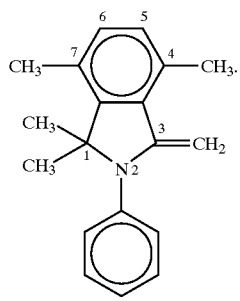

Specific examples of nitrous compounds having general formula (XI) are the following, represented by formula (XIa) corresponding to 1-nitrous-2-naphthol, by formula (XIb) corresponding to 2-nitrous-1-naphthol, by formula (XIc) corresponding to 5-nitrous-6-hydroxy-quinoline, by formula (XId) corresponding to 1-nitrous-2-naphthol-6-propan(1) one and by formula (XIe) corresponding to 10-nitrous-9-phenanthrol:

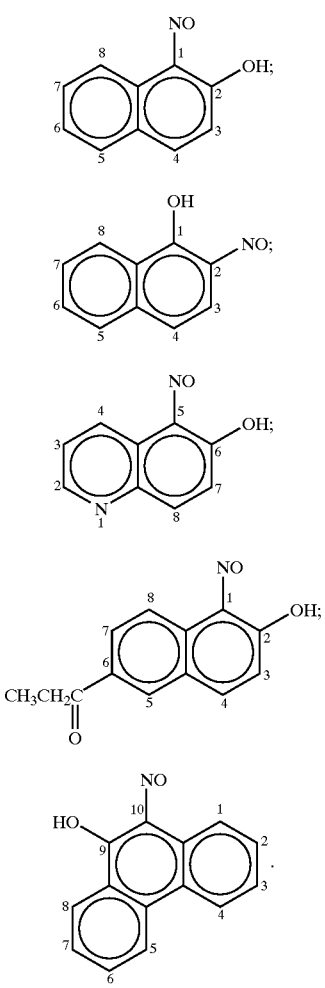

Specific examples of aromatic 1,2-quinone compounds having general formula (XII) are the following, represented by formula (XIIa) corresponding to 1,2-naphthoquinone-4-morpholine, formula (XIIb) corresponding to 1,2-naphthoquinone-4-piperidine and by formula (XIIc) corresponding to 1,2-naphthoquinone-4-(dimethylaniline):

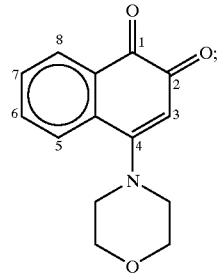

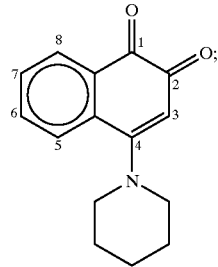

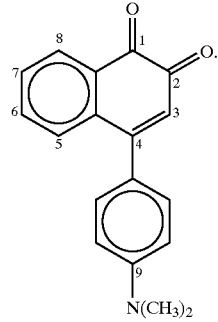

The photochromatic compounds having general formula (I) of the present invention are colourless or slightly yellowish crystalline products.

Their solutions in common organic solvents such as, for example, benzene, toluene, methanol, when not exposed to light sources are colourless or slightly yellow. These solutions, if exposed to a light source, either visible or UV, become blue-coloured, either sky-blue or blue-green. The colouring quickly diminishes when the light source is removed.

The photochromatic compounds having general formula (I) can be applied to the surface or incorporated in mass into the desired articles, using techniques already known in the art and described hereunder.

Some polymeric photochromatic end-articles can be obtained with moulding techniques such as, for example, injection or compression moulding, starting from polymers in which the photochromatic compound having formula (I) is homogeneously dispersed in mass.

Alternatively, the photochromatic compound having general formula (I) can be dissolved in a solvent, together with the polymeric material such as, for example, polymethyl methacrylate, polyvinyl alcohol, polyvinyl butyral, cellulose acetate butyrate or epoxy, polysiloxane, urethane resin. The mixture thus obtained is deposited on a transparent carrier to form, after evaporation of the solvent, a photochromatic coating.

The photochromatic compound having general formula (I) can also be added to a polymerizable monomer such as, for example, a meth(acrylic) or allyl carbonate monomer, so that, after polymerization carried out in the presence of a suitable initiator such as, for example, azo-bis (isobutyronitrile) in the case of the meth(acrylic) monomer or a peroxyketal in the case of the allyl carbonate monomer, they are uniformly incorporated in the resin formed.

Finally, the photochromatic compound having general formula (I) can be applied to a transparent substrate such as, for example, polycarbonate, polymethyl methacrylate or polydiethylene glycol bis(allyl carbonate), by surface impregnation obtained by putting the substrate in contact, at a suitable temperature, with a solution or dispersion containing the photochromatic compound having general formula (I), operating according to the method described, for example, in U.S. Pat. No. 5,130,353.

The photochromatic compounds having general formula (I) of the present invention have the characteristic of being able to be incorporated in mass or using one of the techniques described above, into various organic polymers such as, for example, high density polyethylene, low density polyethylene, ethylene-vinylacetate copolymer, polyether amides, polypropylene, polymethylmethacrylate, polyvinyl alcohol, polyvinyl butyral, cellulose acetate butyrate, epoxy, polysiloxane or urethane resins, polycarbonate, polydiethylene glycol bis(allyl carbonate), polyamides, polyesters, polystyrene, vinyl polychloride, polymethylacrylate, polyethylacrylate, siliconic polymers.

The photochromatic compounds having general formula (I) of the present invention can be optionally used in the presence of the usual additives for organic polymers such as, for example, phenol antioxidants, sterically hindered amines, benzotriazoles, phosphites or phosphonites.

A further object of the present invention therefore relates to polymeric compositions comprising the above polymeric materials and the above photochromatic compounds having general formula (I), optionally in the presence of the above polymeric additives, and the photochromatic articles obtained from their processing.

The photochromatic compounds having general formula (I) of the present invention, have a photochromatic activity also at room temperature and, surprisingly, in some cases, their photochromatic activity is higher than that of products belonging to the group of spiro-indolino-oxazines.

The photochromatic compounds having general formula (I) of the present invention can be used as such, mixed with each other, or combined with other suitable organic photochromatic compounds to obtain, after activation, the formation of different colourings such as, green, brown and grey. Photochromatic compounds belonging to the group of spiro-indolino-oxazines or spiro-pyranes described in the art such as, for example, in U.S. Pat. No. 5,066,818, are particularly useful for the purpose.

The examples provided hereunder for a better understanding of the present invention and for its embodiment are purely illustrative and no way limit the scope of the invention itself.

EXAMPLE 1

Preparation of 1,1,2,4,7-pentamethyl-3-methylene-isoindoline iodide 40 g of acetonylacetone, 12 g of methylamine hydrochloride, 20 ml of water and 12 ml of ethyl alcohol are charged into a 100 ml flask, equipped with a reflux cooler and mechanical stirrer.

The above mixture is heated to 80° C., under a nitrogen atmosphere, for 24 hours. At the end, the mixture is cooled and subsequently extracted with 30 ml of hexane. The aqueous phase obtained is treated with sodium hydroxide at 30% until pH 14 is reached: a yellow-white precipitate is thus formed which is rapidly filtered and washed with 30 ml of water and 10 ml of hexane.

The product is dried under vacuum and conserved in a nitrogen atmosphere: the yield is 23.5 g. This product is identified as 1,2,3,4,7-pentamethyl-isoindoline, by gas-mass (molecular weight=187) and NMR spectrum.

A quantity equal to 23.5 g of the above product is placed in a 100 ml inox steel autoclave together with 20 ml of toluene and 16 g of methyliodide. The autoclave is heated to 85° C. and is maintained at this temperature, under a nitrogen atmosphere, for 6 hours. At the end, the autoclave is cooled to room temperature and the raw product is filtered obtaining a crystalline precipitate which is washed with 20 ml of ethyl acetate and finally with 20 ml of hexane.

35 g of product are obtained, corresponding to 1,1,2,4,7-pentamethyl-3-methylene-isoindoline iodide. The free base, corresponding to Compound (Xa), is identified by gas-mass (molecular weight=201) and the salt by NMR. The NMR data are indicated in Table 1.

TABLE 1

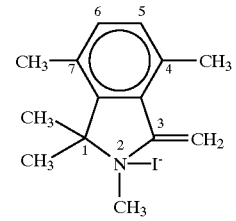

| ¹H | δ (ppm) |
|---|---|
| CH₃ on C1 | 1.74 |
| NCH₃ | 3.83 |
| CH₃ on C3 | 3.17 |
| CH₃ on C4 | 2.46 |
| CH₃ on C7 | 2.67 |
| H5 | 7.17 |
| H6 | 7.37 |

EXAMPLE 2

Preparation of 1,1,4,7-tertamethyl-N-phenyl-3-methylene-isoindoline iodide 46 g of acetonylacetone, 26 g of aniline hydrochloride, 20 ml of water and 12 ml of ethyl alcohol are charged into a 100 ml flask, equipped with a reflux cooler and mechanical stirrer.

The above mixture is heated to 80° C., under a nitrogen atmosphere, for 24 hours. At the end, the mixture is cooled and subsequently extracted with 30 ml of hexane. The aqueous phase obtained is treated with sodium hydroxide at 30% until a pH 14 is reached: a yellow-white precipitate is thus formed which is rapidly filtered and washed with 30 ml of water and 20 ml of hexane.

The product is dried under vacuum and conserved in a nitrogen atmosphere: the yield is 44 g. This product is identified as 1,3,4,7-tetramethyl-N-phenyl-isoindoline, by gas-mass (molecular weight=249) and NMR spectrum.

A quantity equal to 25 g of the above product is placed in a 100 ml inox steel autoclave together with 20 ml of toluene and 18 g of methyliodide. The autoclave is heated to 85° C. and is maintained at this temperature, under a nitrogen atmosphere, for 6 hours. At the end, the autoclave is cooled to room temperature and the raw product is filtered obtaining a crystalline precipitate which is washed with 20 ml of ethyl acetate and finally with 20 ml of hexane.

24 g of product are obtained, corresponding to 1,1,4,7-tetramethyl-N-phenyl-3-methylene-isoindoline iodide. The free base, corresponding to Compound (Xb), is identified by gas-mass (molecular weight=263) and the salt by NMR. The NMR data are indicated in Table 2.

TABLE 2

(structure shown)

| $^1$H | δ (ppm) |
|---|---|
| CH$_3$ on C1 | 1.70 |
| CH$_3$ on C3 | 3.02 |
| CH$_3$ on C4 | 2.51 |
| CH$_3$ on C7 | 2.74 |
| H5 | 7.26 |
| H6 | 7.46 |
| a | 7.65 |
| b | 7.72 |
| c | 7.61 |

TABLE 3

(Ia)

(structure shown)

| $^1$H | δ (ppm) | $^1$H | δ (ppm) |
|---|---|---|---|
| CH$_3$ on C1 | 1.52; 1.55 | H5' | 7.08 |
| NCH$_3$ | 2.25 | H6' | 7.70 |
| CH$_3$ on C4 | 2.26 | H7' | 7.78 |
| CH$_3$ on C7 | 2.48 | H8' | 7.41 |
| H5 | 7.06 | H9' | 7.59 |
| H6 | 7.12 | H10' | 8.64 |
| H2' | 7.48 | — | — |

EXAMPLE 3

Preparation of the Compound Having Formula (Ia)

6.6 g of 1,1,2,4,7-pentamethyl-3-methylene isoindoline iodide obtained as described in Example 1, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xa)], is then separated.

3.5 g of 1-nitrous-2-naphthol [Compound (XIa)] are added to the above organic phase: the mixture obtained is heated to 70° C. and maintained at this temperature, under stirring, under a nitrogen atmosphere, for two hours. The reaction raw product obtained is then purified by passage on a silica gel column eluating with a mixture of heptane/toluene in a ratio of 1/1.

The raw photochromatic product thus obtained is then purified again by crystallization from toluene.

2.6 g of an almost white product are obtained, corresponding to the Compound having formula (Ia) which is identified by gas-mass (molecular weight=356) and NMR spectrum. The NMR data are indicated in Table 3.

EXAMPLE 4

Preparation of the Compound Having Formula (Ib)

5 g of 1,1,4,7-tetramethyl-N-phenyl-3-methylene isoindoline iodide obtained as described in Example 2, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xb)], is then separated.

1.7 g of 1-nitrous-2-naphthol [Compound (XIa)] are added to the above organic phase: the mixture obtained is heated to 70° C. and maintained at this temperature, under stirring, under a nitrogen atmosphere, for two hours. The reaction raw product obtained is then purified by passage on a silica gel column eluating with a mixture of heptane/toluene in a ratio of 1/1.

The raw photochromatic product thus obtained is then purified again by crystallization from toluene.

1.6 g of a yellow crystalline product are obtained, corresponding to the Compound having formula (Ib) which is identified by gas-mass (molecular weight=418) and NMR spectrum. The NMR data are indicated in Table 4.

TABLE 4

(Ib)

| ¹H | δ (ppm) | ¹H | δ (ppm) |
|---|---|---|---|
| CH₃ on C1 | 1.55; 1.64 | H7' | 7.67 |
| CH₃ on C4 | 2.28 | H8' | 7.29 |
| CH₃ on C7 | 2.55 | H9' | 7.42 |
| H5 | 7.13 | H10' | 8.30 |
| H6 | 7.20 | a | 7.21 |
| H2' | 7.58 | b | 7.01 |
| H5' | 7.09 | c | 6.95 |
| H6' | 7.61 | — | — |

EXAMPLE 5

Preparation of Compound (Ic)

5 g of 1,1,2,4,7-pentamethyl-3-methylene isoindoline iodide obtained as described in Example 1, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xa)], is then separated and dried under vacuum.

The dry residue obtained is dissolved in 20 ml of isopropanol to which 2 ml of triethylamine and 2.65 g of 5-nitrous-6-hydroxy-quinoline [Compound (XIc)] are added and the mixture is heated to 70° C., under a nitrogen atmosphere and under stirring, for 4.5 hours. The reaction raw product obtained is then purified by passage on a silica gel column eluating with a mixture of heptane/toluene in a ratio of 1/1.

The raw photochromatic product thus obtained is then purified again by crystallization from toluene.

2 g of a yellow crystalline product are obtained, corresponding to the Compound having formula (Ic) which is identified by gas-mass (molecular weight 357) and NMR spectrum. The NMR data are indicated in Table 5.

TABLE 5

(Ic)

| ¹H | δ (ppm) | ¹H | δ (ppm) |
|---|---|---|---|
| CH₃ on C3 | 1.52; 1.55 | H2' | 7.44 |
| NCH₃ | 2.21 | H5' | 7.29 |
| CH₃ on C4 | 2.21 | H6' | 7.94 |
| CH₃ on C7 | 2.49 | H8' | 8.80 |
| H5 | 7.02 | H9' | 7.46 |
| H6 | 7.13 | H10' | 8.92 |

EXAMPLE 6

Preparation of Compound (Id)

5 g of 1,1,2,4,7-pentamethyl-3-methylene isoindoline iodide obtained as described in Example 1, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xa)], is then separated and dried under vacuum.

The dry residue obtained is dissolved in 20 ml of isopropanol to which 2 ml of triethylamine and 3.4 g of 1-nitrous-2-naphthol-6-propan(1)one [Compound (XId)] are added: the mixture is heated to 70° C. and maintained at this temperature, under stirring, under a nitrogen atmosphere, for three hours. The reaction raw product obtained is then purified by passage on a silica gel column eluating with a mixture of heptane/toluene in a ratio of 1/1.

The raw photochromatic product thus obtained is then purified again by crystallization from toluene.

2 g of a yellow-white crystalline product are obtained, corresponding to the Compound having formula (Id) which is identified by gas-mass (molecular weight =412) and NMR spectrum. The NMR data are indicated in Table 6.

TABLE 6

(Id)

| ¹H | δ (ppm) | ¹H | δ (ppm) |
|---|---|---|---|
| CH₃ on C1 | 1.50; 1.55 | H5' | 7.12 |
| NCH₃ | 2.22 | H6' | 7.81 |

TABLE 6-continued (Id)

[Structure: 1,1,2,4,7-pentamethyl isoindoline spiro-linked to naphthoxazine with COCH₂CH₃ substituent at position 8']

| ¹H | δ (ppm) | ¹H | δ (ppm) |
|---|---|---|---|
| CH₃ on C4 | 2.22 | H7' | 8.42 |
| CH₃ on C7 | 2.48 | H9' | 8.13 |
| H5 | 7.04 | H10' | 8.67 |
| H6 | 7.12 | a | 3.13 |
| H2' | 7.47 | b | 1.28 |

EXAMPLE 7

Preparation of Compound (Ie)

5 g of 1,1,2,4,7-pentamethyl-3-methylene isoindoline iodide obtained as described in Example 1, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xa)], is then separated.

2 ml of aqueous ammonia at 30% and 3.6 g of 1,2-naphthoquinone-4-morpholine [Compound (XIIa)] are added to the above organic phase and the mixture is heated to 70° C., in an autoclave, under a nitrogen atmosphere and under stirring, for two hours. The reaction raw product obtained is then purified by passage on a silica gel column eluating with a mixture of heptane/toluene in a ratio of 1/1.

The raw photochromatic product thus obtained is then purified again by crystallization from toluene.

0.8 g of a yellow-white crystalline product are obtained, corresponding to the Compound having formula (Ie) which is identified by gas-mass (molecular weight=441) and NMR spectrum. The NMR data are indicated in Table 7.

TABLE 7

(Ie)

[Structure: 1,1,2,4,7-pentamethyl isoindoline spiro-linked to naphthoxazine with morpholine substituent at position 6']

| ¹H | δ (ppm) | ¹H | δ (ppm) |
|---|---|---|---|
| CH₃ on C1 | 1.49; 1.55 | H5' | 6.66 |
| NCH₃ | 2.27 | H7' | 8.08 |
| CH₃ on C4 | 2.22 | H8' | 7.38 |
| CH₃ on C7 | 2.46 | H9' | 7.56 |
| H5 | 7.04 | H10' | 8.62 |
| H6 | 7.11 | a | 3.11 |
| H2' | 7.34 | b | 3.94 |

EXAMPLE 8

Preparation of Compound (If)

6.6 g of 1,1,2,4,7-pentamethyl-3-methylene isoindoline iodide obtained as described in Example 1, 10 ml of water, 3 ml of ethyl alcohol, 30 ml of toluene and 2 g of sodium hydroxide dissolved in 5 ml of water are charged into a 100 ml flask, equipped with a reflux cooler and mechanical stirrer.

The above mixture is stirred for 10 minutes under a nitrogen atmosphere and the organic phase containing the free base [Compound (Xa)], is then separated.

3.5 g of 2-nitrous-1-naphthol [Compound (XIb)] are added to the above organic phase: the mixture obtained is heated to 70° C. and maintained at this temperature, under stirring, under a nitrogen atmosphere, for two hours. The reaction raw product obtained is then purified by passage on a silica gel column eluating with a mixture of heptane/toluene in a ratio of 1/1.

The raw photochromatic product thus obtained is then purified again by crystallization from toluene.

2.0 g of a yellow-white crystalline product are obtained, corresponding to the Compound having formula (If) which is identified by gas-mass (molecular weight=356) and NMR spectrum. The NMR data are indicated in Table 8.

TABLE 8

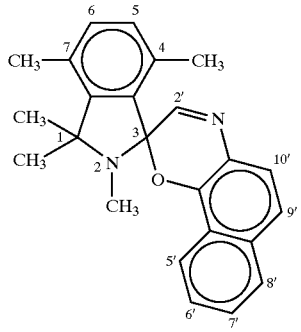

(If)

| $^1$H | δ (ppm) | $^1$H | δ (ppm) |
|---|---|---|---|
| CH$_3$ on C1 | 1.50; 1.61 | H5' | 7.79 |
| NCH$_3$ | 2.20 | H6' | 7.38 |
| CH$_3$ on C4 | 2.23 | H7' | 7.45 |
| CH$_3$ on C7 | 2.49 | H8' | 8.10 |
| H5 | 7.05 | H9' | 7.58 |
| H6 | 7.14 | H10' | 7.43 |
| H2' | 7.41 | — | — |

EXAMPLE 9

Evaluation of the Photochromatic Activity

The photochromatic activity is evaluated in methanol and toluene, at 20° C., of Compounds (Ia)–(If) obtained as described above in Examples 3–8.

Solutions are prepared at a concentration equal to about $10^{-4}$ M (the exact concentrations are indicated in Table 9) of the various Compounds (Ia)–(If) in the two solvents and subsequently 1.3 ml of each solution is placed, individually, in a 1 cm quartz cell having a square base inlet.

The quartz cell containing the solution is introduced into a Peltier temperature control system (HP accessory—HP 89090A), with the possibility of magnetic stirring during the measuring, and is irradiated from above with a Philips UVA lamp with an irradiance equal to 9 Watt/cm$^2$ supported on the cell itself. The irradiance time varies from sample to sample (60"–180") to guarantee the maximum degree of colouring of the solution.

The spectrum of the solution is recorded before and after irradiation between 400 nm and 700 nm with a Hewlett Packard HP 8452A photodiode spectrophotometer.

The following data are determined by means of a mathematical calculation carried out with the program 123v5w of Lotus based on the tristimulus theory:

(a) (ΔY) which indicates the difference between the luminous transmittance (Y) of the solution before and after irradiation and represents the photochromatic activity of the compound analyzed at the concentrations indicated in Table 9;

(b) ΔL*, Δa* and Δb* which correspond to the variation of the colourimetric coordinates of the above solutions CIE 1976 (L*, a* and b*), corresponding to the brightness or luminosity (L*), the red-green coordinate (a*) and the yellow-blue coordinate (b*), before and after irradiation. The data obtained are indicated in Table 9.

A further explanation of the above values and information relating to these can be found, for example, in "Color Science: Concepts and Methods, Quantitative data and Formulae" (1982), G. Wyszecki and W. S. Stiles, 2nd Ed., New York.

TABLE 9

Photochromatic activity and colorimetric data at 20° C.

| | METHANOL | | | | | TOLUENE | | | | |
|---|---|---|---|---|---|---|---|---|---|---|
| Compound | Conc. ($10^{-4}$M) | ΔY | ΔL* | Δa* | Δb* | Conc. ($10^{-4}$M) | ΔY | ΔL* | Δa* | Δb* |
| (Ia) | 1.016 | 64.43 | −37.58 | −28.98 | −41.08 | 0.976 | 27.86 | −12.61 | −6.29 | −17.66 |
| (Ib)** | — | — | — | — | — | — | — | — | — | — |
| (Ic) | 1.014 | 75.71 | −55.26 | 32.28 | −64.96 | 0.969 | 66.24 | −38.01 | −0.67 | −52.94 |
| (Id) | 1.010 | 73.94 | −53.19 | 1.23 | −56.22 | 1.034 | 76.32 | −50.96 | −1.77 | −62.16 |
| (Ie) | 0.998 | 23.02 | −12.91 | −11.14 | −14.85 | 1.088 | 8.51 | −3.61 | −0.53 | 4.57 |
| (If) | 1.017 | 1.26 | −0.52 | −0.84 | −0.74 | 1.084 | 26.84 | −12.25 | 11.09 | −17.37 |

(Ib)**: Compound (Ib) does not have activity at room temperature (20° C.); it has a blue colouring when irradiated at 0° C.

What is claimed is:
1. Photochromatic compounds belonging to the group of spiro-isoindolino-oxazines having general formula (I):

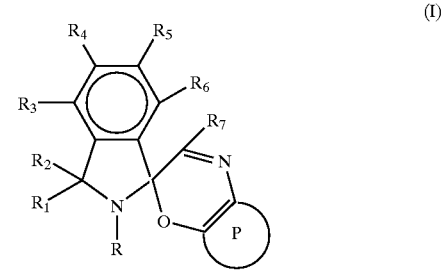

(I)

wherein:
  a) R represents a linear or branched C$_1$–C$_{10}$ alkyl group, said alkyl group optionally substituted with 1–10 halogen atoms selected from fluorine, chlorine and bromine, or with hydroxyl groups, linear or branched C₁–C₆ alkoxyl groups, carboxyl groups, cyano groups, or with a 2,2,6,6-tetramethylpiperidine group; a linear or branched C₂–C₆ alkenyl group; an aryl group selected from phenyl, biphenyl and naphthyl, said aryl group optionally substituted with linear or branched (C₁–C₆) alkoxyl groups, carboxyl groups, amine groups, N,N-dialkyl (C₁–C₆) amine groups; a benzyl group;

b) R₁ and R₂, the same or different, represent a linear or branched C₁–C₁₀ alkyl group, said alkyl group optionally substituted with 1–10 halogen atoms selected from fluorine, chlorine and bromine, or with hydroxyl groups, linear or branched C₁–C₆ alkoxyl groups, carboxyl groups, cyano groups; a linear or branched C₂–C₁₀ alkenyl group; a benzyl group; a linear or branched C₁–C₆ alkoxyl group; an N-alkyl (C₁–C₆) amine group; an N,N-dialkyl (C₁–C₆) amine group; or R₁ and R₂, considered jointly with the carbon atom to which they are bound, represent a C₄–C₁₀ cycloalkyl group, said cycloalkyl group optionally substituted with halogen atoms selected from fluorine, chlorine and bromine, or with hydroxyl groups, linear or branched C₁–C₆ alkoxyl groups, carboxyl groups, cyano groups, amine groups, N-alkyl (C₁–C₆) amine groups, N,N-dialkyl (C₁–C₆) amine groups, an N,N-dialkyl (C₁–C₆) amide group; a cyano group; an aryl group selected from phenyl and biphenyl;

c) R₃, R₄, R₅ and R₆, the same or different, represent a hydrogen atom; a halogen atom selected from fluorine, chlorine, bromine and iodine; a linear or branched C₁–C₆ alkyl group, said alkyl group optionally substituted with 1–6 halogen atoms selected from fluorine, chlorine and bromine, or with hydroxyl groups, linear or branched C₁–C₆ alkoxyl groups, cyano groups; a benzyl group; a hydroxyl group; a linear or branched C₁–C₆ alkoxyl group; an amine group; an N-alkyl (C₁–C₆) amine group; an N,N-dialkyl (C₁–C₆) amine group; a piperidine, piperazine or morpholine group; a C₁–C₆ carboxyalkyl group; a C₂–C₆ carboxyalkenyl group; a carboxyamide group; an N-alkyl (C₁–C₆) carboxyamide group; an N,N-dialkyl (C₁–C₆) carboxyamide group; a cyano group; a nitro group; a sulfonic group; an aryl group selected from phenyl, biphenyl and naphthyl, said aryl group optionally substituted with N,N-dialkyl (C₁–C₆) amine groups, linear or branched C₁–C₆ alkoxyl groups, hydroxyl groups, linear or branched C₁–C₆ alkyl groups; an acyl group of the alkyl ketone, aryl ketone or benzyl ketone type; a linear or branched C₂–C₆ alkenyl group, said alkenyl group optionally subsituted with one or two N,N-dialkyl (C₁–C₆)-4-aniline groups; an N-2,3-dihydroindoline group; a linear or branched C₁–C₆ thioether group;

d) two consecutive substituents between R₃ and R₆, can represent the condensation points with other aromatic, heterocyclic or quinone rings;

e) R₇ represents a hydrogen atom; a halogen atom selected from fluorine, chlorine and bromine; a linear or branched C₁–C₆ alkyl group; a linear or branched C₁–C₆ alkoxyl group; a phenyl group; a phenoxyl group;

f) P represents a monocyclic or polycyclic aromatic nucleus, belonging to one of the following types: benzene represented by general formula (II); naphthalene represented by general formula (III); quinoline represented by general formula (IV); isoquinoline represented by general formula (V); cumarine represented by general formula (VI); quinazoline represented by general formula (VII); phenanthrene represented by general formula (VIII); anthracene represented by general formula (IX):

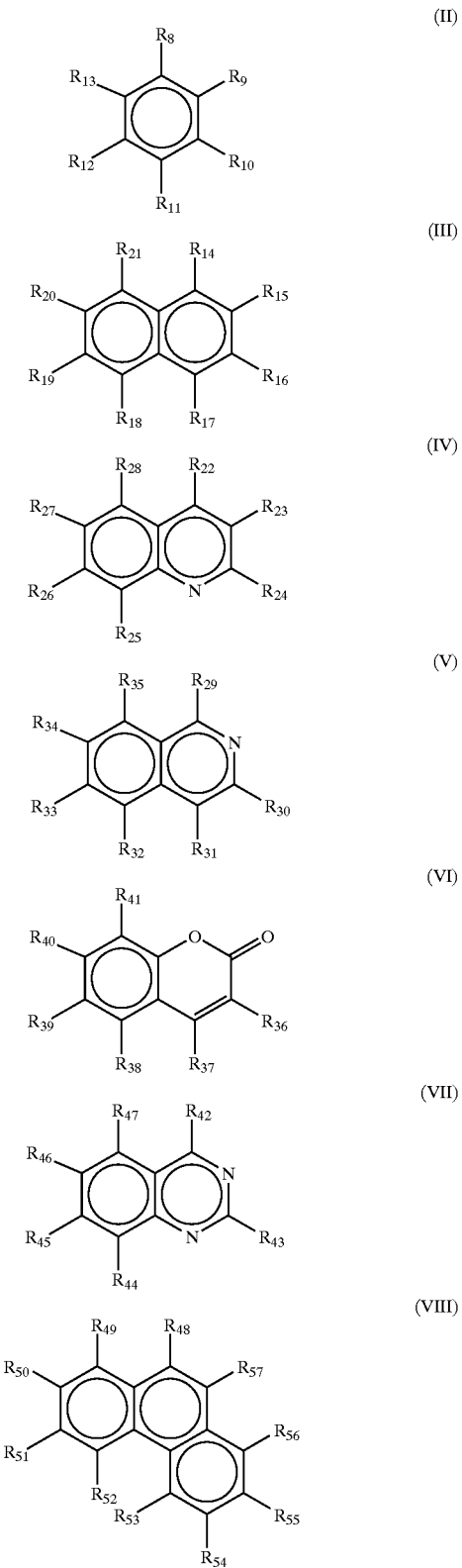

-continued

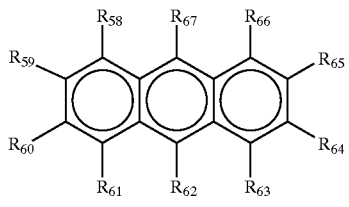

(IX)

wherein:
at least two adjacent substituents between $R_8$ and $R_{13}, R_{14}$ and $R_{21}, R_{22}$ and $R_{28}, R_{30}$ and $R_{35}, R_{36}$ and $R_{41}, R_{44}$ and $R_{47}, R_{48}$ and $R_{57}, R_{58}$ and $R_{67}$, represent the condensation points with the oxazine ring, the other substituents having the same meaning described under point c).

2. The photochromatic compounds belonging to the group of spiro-isoindolino-oxazines having general formula (I) according to claim 1, wherein:

R represents one of the following groups: methyl, ethyl, isopropyl, 2-allyl, 2-hydroxyethyl, 2-carboxymethyl, phenyl, 4-N,N-dimethylaminoaniline, 4-methoxybenzene, 4-cyanobenzene;

$R_1$ and $R_2$, the same or different, represent a methyl or phenyl group; or considered jointly with the carbon atom to which they are bound, represent a cyclohexyl group;

$R_3$, $R_4$, $R_5$ and $R_6$, the same or different, represent a hydrogen atom, a fluorine atom, a chlorine atom, a bromine atom, or one of the following groups: methyl, isopropyl, hydroxyl, methoxyl, N,N-dimethylamine, piperidine, morpholine, carboxyl, carboxymethyl, N,N-dimethylcarboxyamide, cyano, nitro, methylketone, phenylketone, phenyl;

$R_7$ represents a hydrogen atom, a chlorine atom, a bromine atom, a methyl group or a phenyl group;

P represents one of the groups having general formula (II) to (IX), wherein:
i) two adjacent substituents between $R_8$ and $R_{13}$, $R_{14}$ and $R_{21}$, $R_{22}$ and $R_{28}$, $R_{30}$ and $R_{35}$, $R_{36}$ and $R_{41}$, $R_{44}$ and $R_{47}$, $R_{48}$ and $R_{57}$, $R_{58}$ and $R_{67}$, independently represent the condensation points with the oxazine ring and the other substituents each independently represent a hydrogen atom, a fluorine atom, a chlorine atom, a bromine atom, or one of the following groups: methyl, isopropyl, hydroxyl, methoxyl, 2-hydroxyethyl, 2-allyl, piperidine, morpholine, N,N-dimethylamine, carboxyl, carboxymethyl, N,N-dimethylcarboxyamide, cyano, nitro, methylketone, ethylketone, phenylketone, methylthiol;
ii) two adjacent substituents between $R_8$ and $R_{13}$, $R_{14}$ and $R_{21}$, $R_{22}$ and $R_{28}$, $R_{30}$ and $R_{35}$, $R_{36}$ and $R_{41}$, $R_{44}$ and $R_{47}$, $R_{48}$ and $R_{57}$, $R_{58}$ and $R_{67}$, different from those specified under point i), represent the condensation points with a benzene or quinone ring.

3. The photochromatic compounds belonging to the group of spiro-isoindolino-oxazines having general formula (I) according to claim 1, consisting of the compound having formula (Ia):

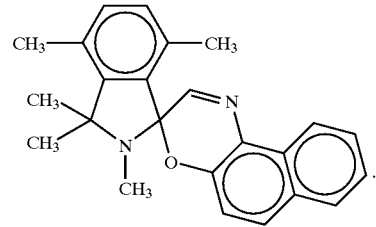

(Ia)

4. The photochromatic compounds belonging to the group of spiro-isoindolino-oxazines having general formula (I) according to claim 1, consisting of the compound having formula (Ib):

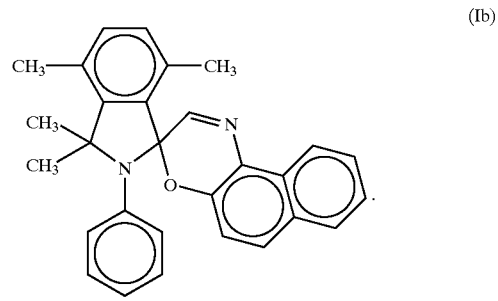

(Ib)

5. The photochromatic compounds belonging to the group of spiro-isoindolino-oxazines having general formula (I) according to claim 1, consisting of the compound having formula (Ic):

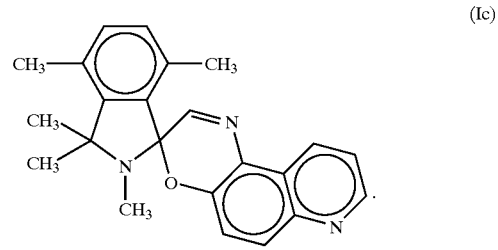

(Ic)

6. The photochromatic compounds belonging to the group of spiro-isoindolino-oxazines having general formula (I) according to claim 1, consisting of the compound having formula (Id):

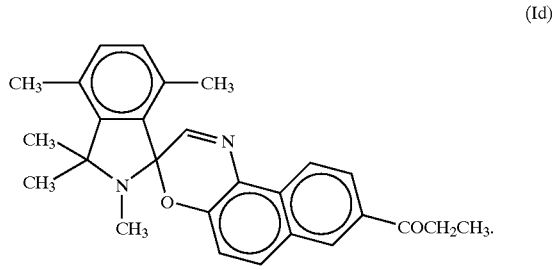

(Id)

7. The photochromatic compounds belonging to the group of spiro-isoindolino-oxazines having general formula (I) according to claim 1, consisting of the compound having formula (Ie):

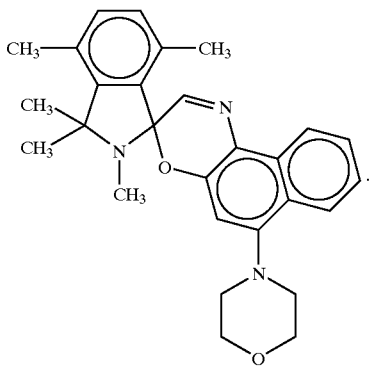

(Ie)

8. The photochromatic compounds belonging to the group of spiro-isoindolino-oxazines having general formula (I) according to claim 1, consisting of the compound having formula (If):

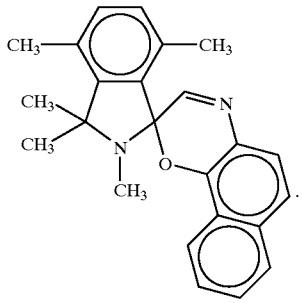

(If)

9. A process for the preparation of the photochromatic compounds belonging to the group of spiro-isoindolino-oxazines having general formula (I) according to claim 1, comprising the condensation of isoindoline compounds having general formula (X):

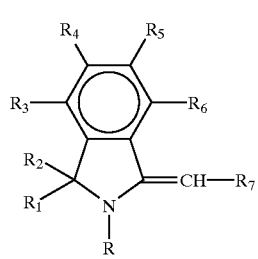

(X)

wherein the substituents from R to $R_7$ have the same meanings defined above, with nitrous compounds having general formula (XI):

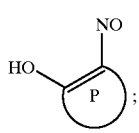

(XI)

or with aromatic 1,2-quinones having general formula (XII):

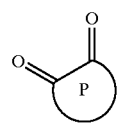

(XII)

wherein P has the same meanings defined above.

10. The process according to claim 9, wherein the condensation reaction between the isoindoline compounds having general formula (X) and the nitrous compounds having general formula (XI), indicated in Scheme 1:

SCHEME 1

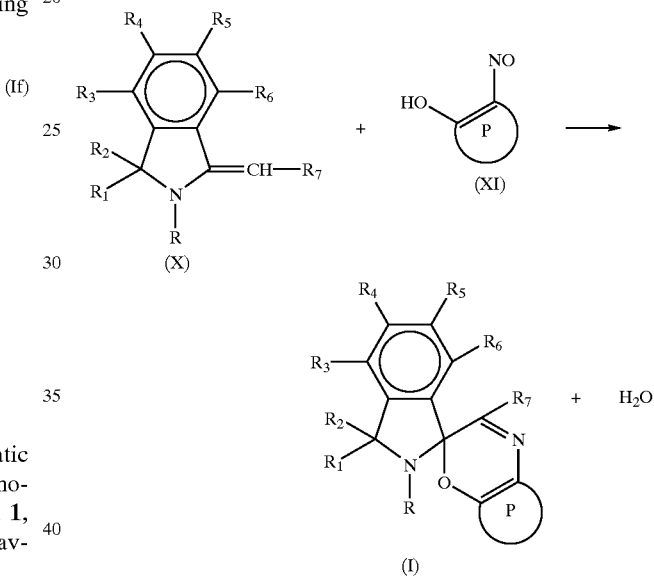

is carried out in the presence of an inert organic solvent, or a mixture of inert organic solvents, at a temperature ranging from 50° C. to 100° C., for a time ranging from 1 hour to 10 hours.

11. The process according to claim 10, wherein the inert organic solvent is selected from ethyl alcohol, isopropanol, toluene, or their mixtures.

12. The process according to claim 10, wherein the reaction temperature is between 60° C. and 75° C.

13. The process according to claim 10, wherein the reaction time is between 2 hours and 5 hours.

14. The process according to claim 9, wherein the condensation reaction between the isoindoline compounds having general formula (X) and the aromatic 1,2-quinones having general formula (XII), indicated in Scheme 2:

SCHEME 2

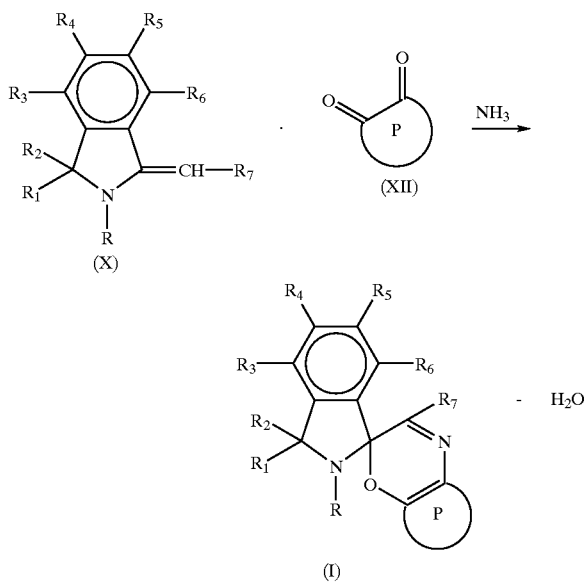

is carried out in the presence of an inert organic solvent, or a mixture of inert organic solvents, and in the presence of aqueous ammonia at 30%, at a temperature ranging from 50° C. to 100° C., for a time ranging from 1 hour to 10 hours.

15. The process according to claim 14, wherein the inert organic solvent is selected from ethyl alcohol, isopropanol, toluene, or their mixtures.

16. The process according to claim 14, wherein the reaction temperature is between 60° C. and 75° C.

17. The process according to claim 14, wherein the reaction time is between 2 hours and 3 hours.

18. Polymeric compositions comprising at least one photochromatic compound having general formula (I) according to claim 1, and at least one organic polymer selected from high density polyethylene, low density polyethylene, ethylene-vinylacetate copolymer, polyether amides, polypropylene, polymethylmethacrylate, polyvinyl alcohol, polyvinyl butyral, cellulose acetate butyrate, epoxy, polysiloxane or urethane resins, polycarbonate, polydiethylene glycol bis(allyl carbonate), polyamides, polyesters, polystyrene, vinyl polychloride, polymethylacrylate, polyethylacrylate, siliconic polymers.

19. The polymeric compositions according to claim 18, comprising additives for organic polymers selected from phenol antioxidants, sterically hindered amines, benzotriazoles, phosphites or phosphonites.

20. Photochromatic articles obtained from the processing of the polymeric compositions according to claim 18.

21. Mixtures comprising at least one photochromatic compound having general formula (I) according to claim 1 and at least one organic photochromatic compound belonging to the group of spiro-indolino-oxazines or spiro-pyranes.

* * * * *